United States Patent [19]

Umezawa et al.

[11] 4,326,054
[45] Apr. 20, 1982

[54] CLEOMYCINS AND PROCESS FOR PRODUCING SAME

[75] Inventors: Hamao Umezawa, Tokyo; Tomohisa Takita, Asaka; Akio Fujii, Kamakura; Yasuhiko Muraoka, Kitamoto; Mamoru Kunishima, Tokorozawa, all of Japan

[73] Assignee: Zaidan Hojin Biseibutsu Kagaku Kenkyu Kai, Tokyo, Japan

[21] Appl. No.: 167,439

[22] Filed: Jul. 9, 1980

[30] Foreign Application Priority Data

Jul. 19, 1979 [JP] Japan .................... 54-90951

[51] Int. Cl.$^3$ ..................... C07H 11/02; C07H 13/12
[52] U.S. Cl. ................. 536/17 R; 424/180; 260/112.5 R; 536/4
[58] Field of Search .............. 260/112.5 R; 536/17 R, 536/4

[56] References Cited

U.S. PATENT DOCUMENTS

| | | | |
|---|---|---|---|
| 3,846,400 | 11/1974 | Umezawa et al. | 260/112.5 R |
| 3,922,262 | 11/1975 | Umezawa et al. | 260/112.5 R |
| 3,960,834 | 6/1976 | Umezawa et al. | 536/17 R |
| 3,984,390 | 10/1976 | Umezawa et al. | 536/17 R |
| 4,195,018 | 3/1980 | Takita et al. | 260/112.5 R |

OTHER PUBLICATIONS

Maeda et al., "Jour. Antibiotics", vol. 9, 1956, pp. 82-85.
Argoudelis et al., "Jour. Antibiotics", vol. 24, 1971, pp. 543-556.
Ito et al., "Jour. Antibiotics", vol. 24, 1971, pp. 727-731.
Ohashi et al., "Agr. Biol. Chem.", vol. 37, (10), 1973, pp. 2387-2391.
Kawaguchi et al., "Jour. Antibiotics", vol. 30, 1977, pp. 779-788.
Konishi et al., "Jour. Antibiotics", vol. 30, 1977, pp. 789-804.
Takasawa et al., "Jour. Antibiotics", vol. 28, 1975, pp. 366-370, 662-666.
Kawamoto et al., "Jour. Antibiotics", vol. 28, 1975, pp. 358-365.
"Jour. Antibiotics", vol. 31, 1978, pp. 801-803.

*Primary Examiner*—Johnnie R. Brown
*Attorney, Agent, or Firm*—Schuyler, Banner, Birch, McKie & Beckett

[57] ABSTRACT

Novel antibiotics cleomycins represented by the formula

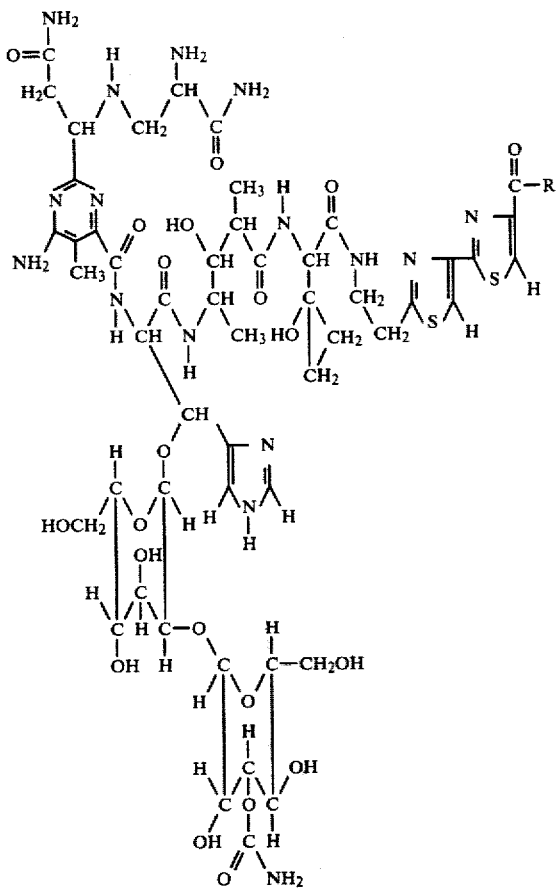

wherein R is a terminal amino residue of the cleomycin. These compounds are useful as a chemotherapeutic agent for treating cancer and bacterial infections.

8 Claims, 8 Drawing Figures

CLEOMYCINS AND PROCESS FOR PRODUCING SAME

BACKGROUND OF THE INVENTION

The present invention relates to cleomycins, antibiotics belonging to the phleomycin-bleomycin group, which have antitumoral and antimicrobial activities and are useful as a chemotherapeutic agent for treating cancer and bacterial infections.

As antibiotics belonging to the phleomycin-bleomycin group the followings are known: bleomycins recovered in a known way from a liquid culture medium of *Strepmyces verticillus* [Umezawa, et al., Journal of Antibiotics, 19 210 (1966)]; bleomycins produced by use of a culture medium admixed with an amino compound as a precursor (U.S. Pat. Nos. 3,846,400 and 4,195,018); bleomycins described in DT-OS 2,828,933; bleomycins N-substituted at the terminal amine (U.S. Pat. No. 3,922,262); phleomycins produced by *Streptmyces verticillus* 843-1 ATCC 21890 [Umezawa, et al., Journal of Antibiotics, A9, 82 (1956)]; zorbamycin produced by *Streptmyces bikiniensis* var. *zorbonesis* [Argoudelis, et al., Journal of Antibiotics, 24, 543 (1971)]; YA-56 substance produced by *Streptmyces humidus* var. *antitumoris* [Furumai et al., Journal of Antibiotics, 24, 727 (1971)]; tallysomycin produced by an actinomycete, Streptoalloteichus [Kawaguchi et al., Journal of Antibiotics, 30, 779 (1977)]; platomycin produced by an actinomyces, *Streptosporangium violaceochromogenes* sub. sp. *globophilum* [Takazawa et al., Journal of Antibiotics 28, 662 (1975)]; zorbonomycin produced by *Streptomyces bikiniensis* var. zorbonensis [Argoudelis et al., Journal of Antibiotics, 24, 543 (1971)]; and victomycin produced by *Streptosporangium violaceochromogenes* [Kawamoto et al., Journal of Antibiotics, 28, 358 (1975)].

SUMMARY OF THE INVENTION

As a result of extensive studies on novel antibiotics of the Phleomycin-Bleomycin group, the present inventors discovered certain compounds, namely cleomycins, which have the partial structure

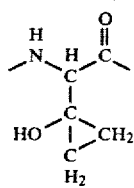

in place of the threonine group in the partial structure

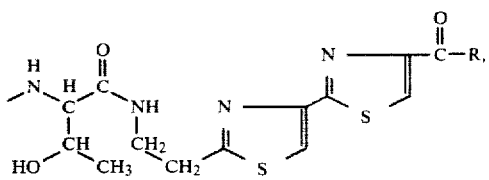

which is present in the bleomycin skeleton, and further found that said compounds have antitumoral and antimicrobial activities, whereby they have accomplished this invention.

BRIEF EXPLANATION OF DRAWINGS

In the accompanying drawings.

DETAILED EXPLANATION OF THE INVENTION

Figure 1:
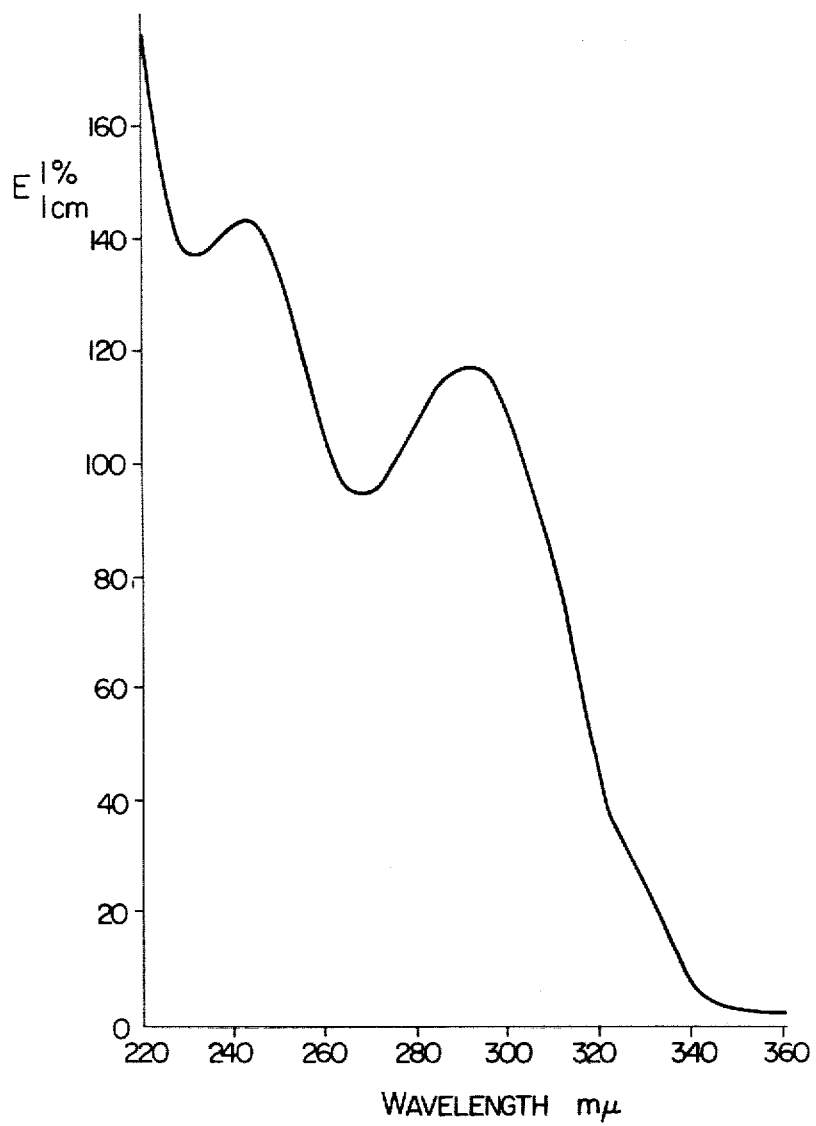
FIG. 1 illustrates the ultraviolet absorption curve of 3-[(S)-1'-phenylethylamino]propylaminocleomycin (Compound No. 33) hydrochloride (copper-containing form) in distilled water, FIG. 2 the ultraviolet absorption curve of 3-[N-methyl-N-(3-aminopropyl)]aminopropylaminocleomycin (Compound No. 20) hydrochloride (copper-free form) in 0.1 N hydrochloric acid, FIG. 3 the ultraviolet absorption curve of 3-[(S)-1'-phenylethylamino]propylaminocleomycin (Compound No. 33) hydrochloride (copper-free-form) in 0.1 N hydrochloric acid, FIG. 4 the infrared absorption curve determined by the potassium bromide tablet method of 3-[N-methyl-N-(3-aminopropyl)]aminopropylaminocleomycin (Compound No. 20) hydrochloride (copper-containing form), FIG. 5 the infrared absorption curve determined by the potassium bromide tablet method of 3-[(S)-1'-phenylethylamino]propylaminocleomycin (Compound No. 33) hydrochloride (copper-containing form), FIG. 6 the infrared absorption curve determined by the potassium bromide tablet method of 3-[N-methyl-N-(3-aminopropyl)]aminopropylaminocleomycin (Compound No. 20) hydrochloride (copper-free form), FIGS. 7 and 8 the infrared absorption curve determined by potassium bromide tablet method and the proton NMR curve (in $D_2O$), respectively, of 3-[(S)-1'-phenylethylamino]propylaminocleomycin (Compound No. 33) sulfate (copper-free form).
Figure 2:
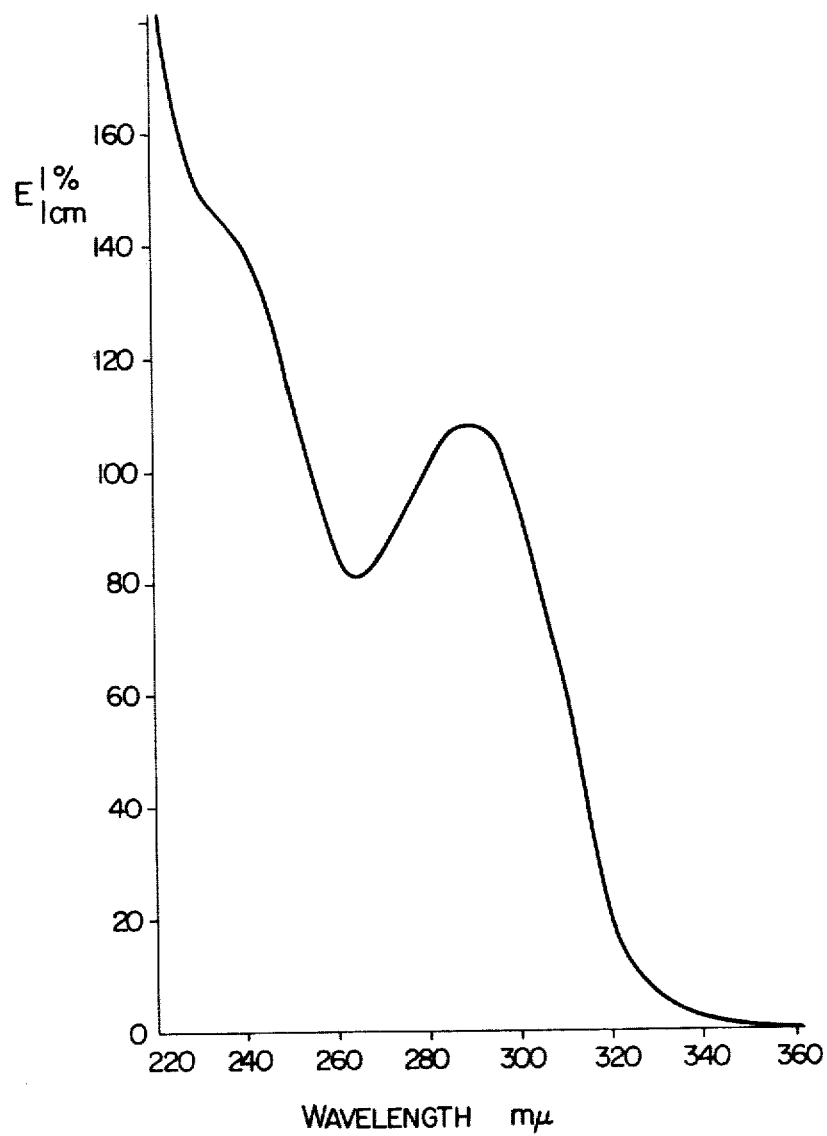
Figure 3:
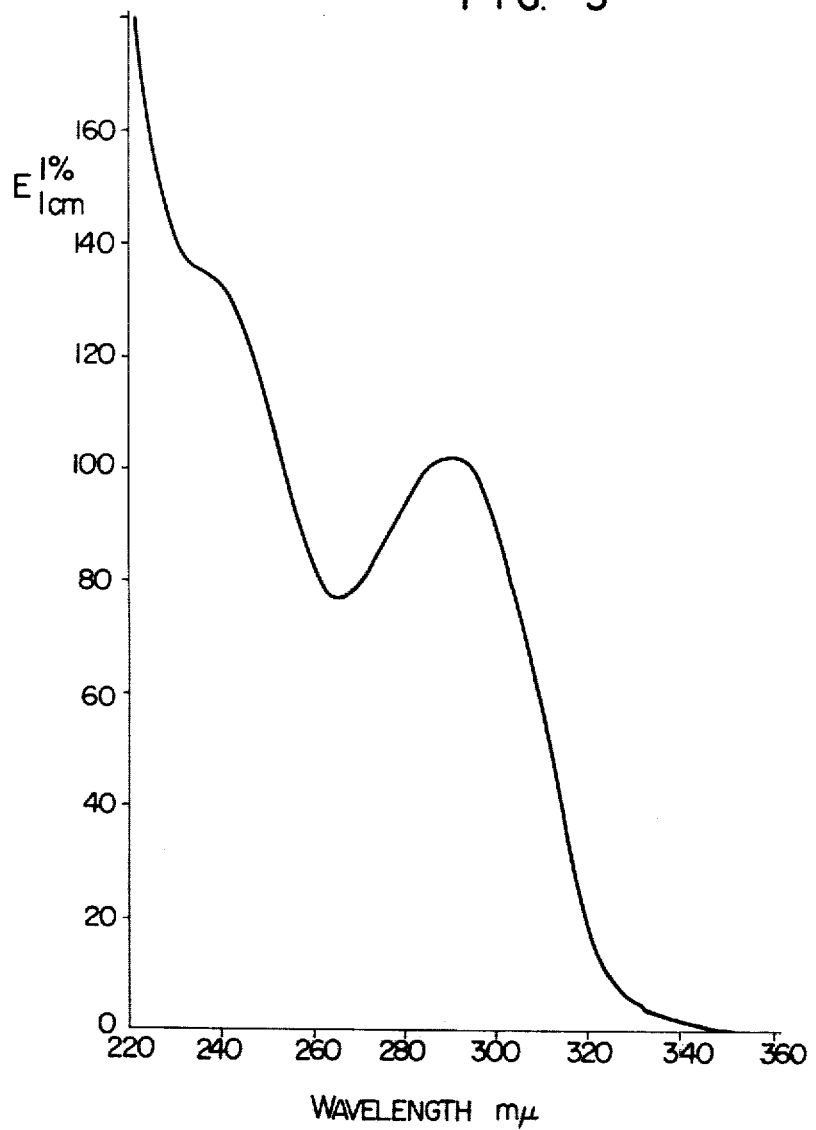
Figure 4:
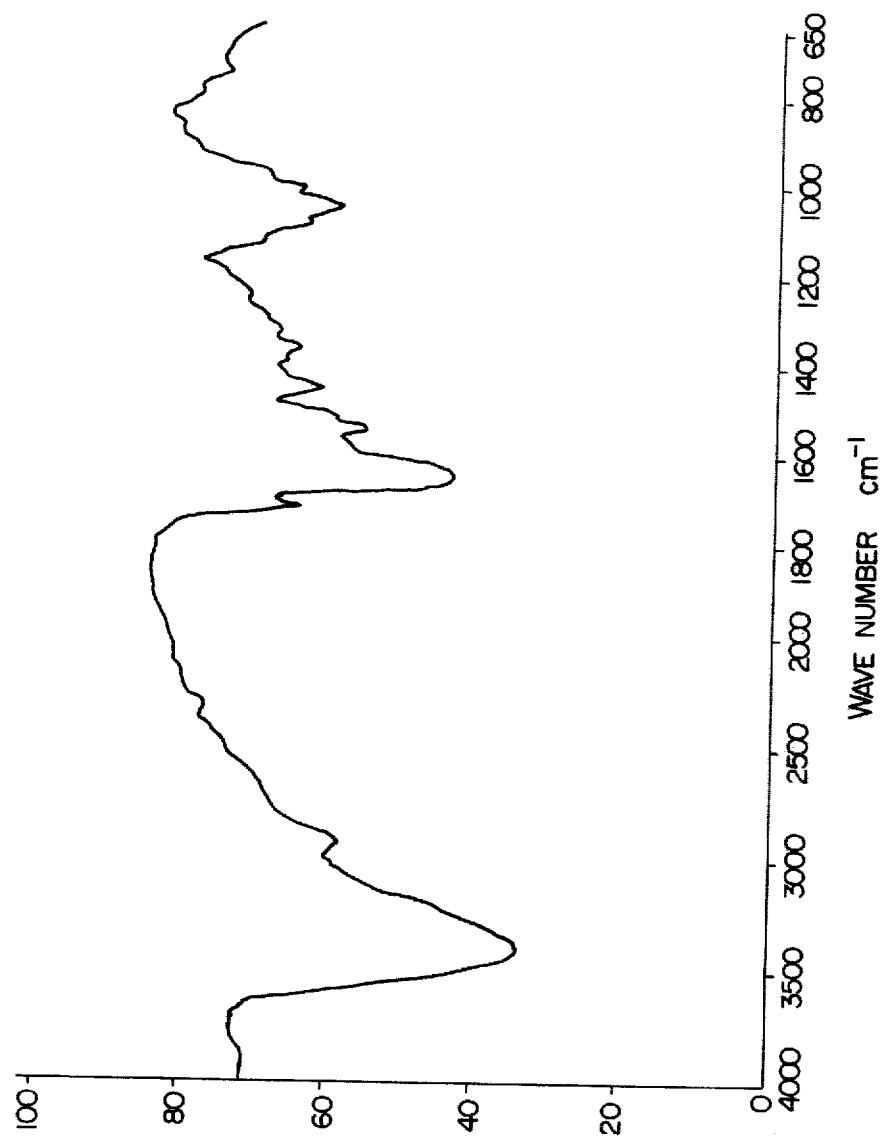
Figure 5:
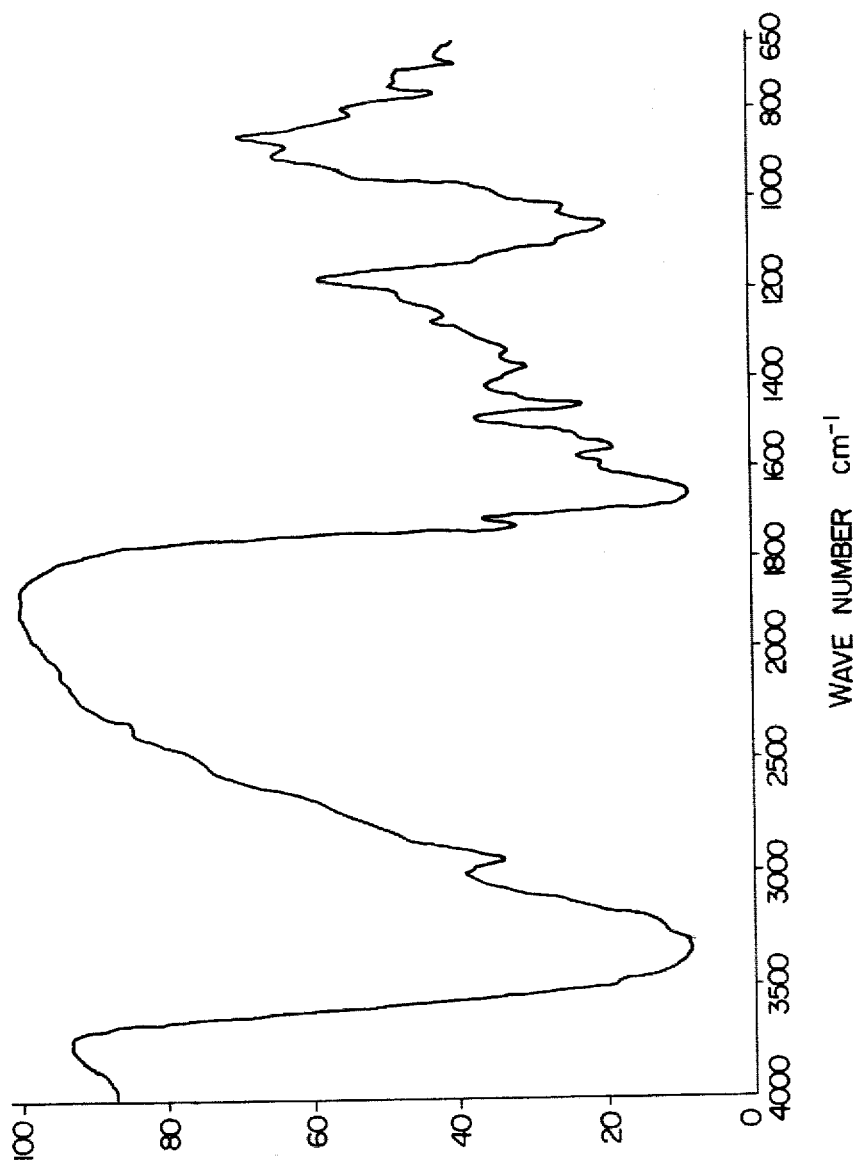
Figure 6:
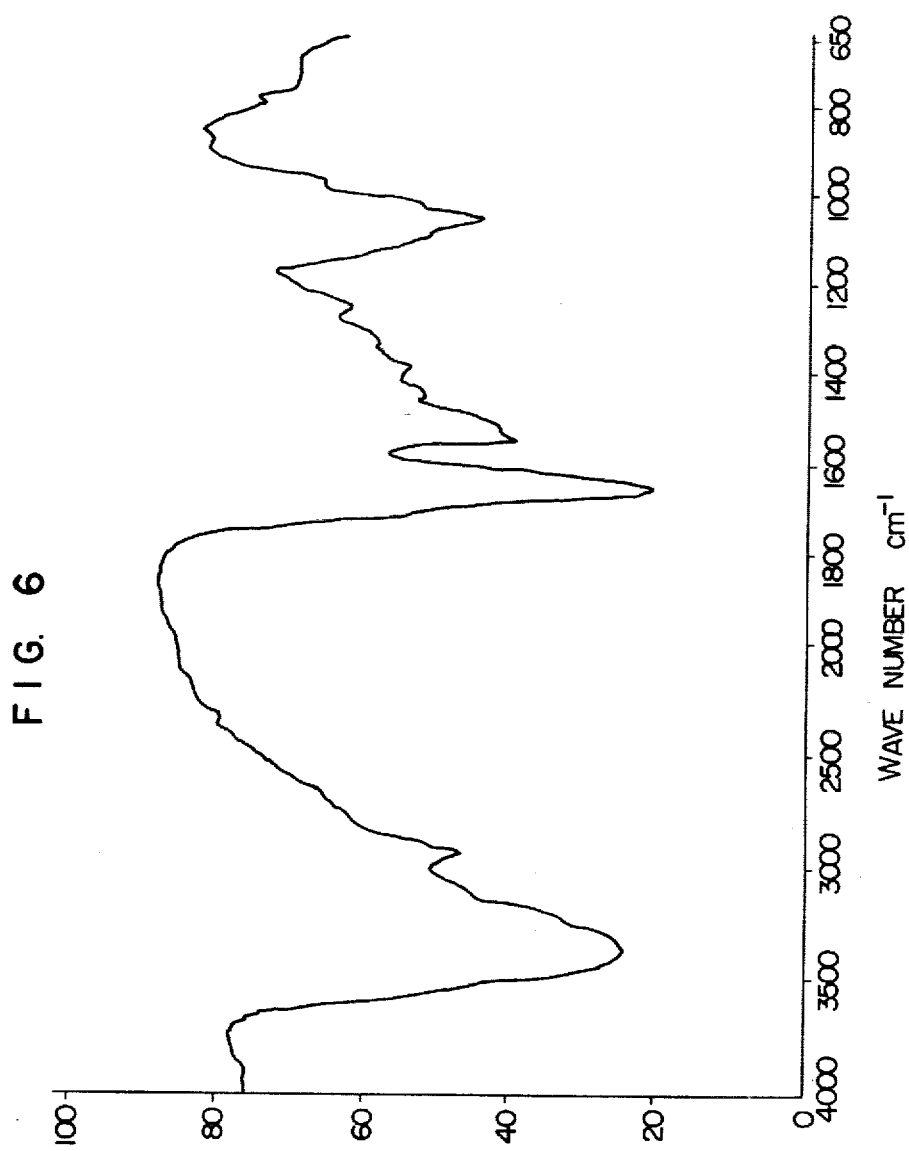
Figure 7:
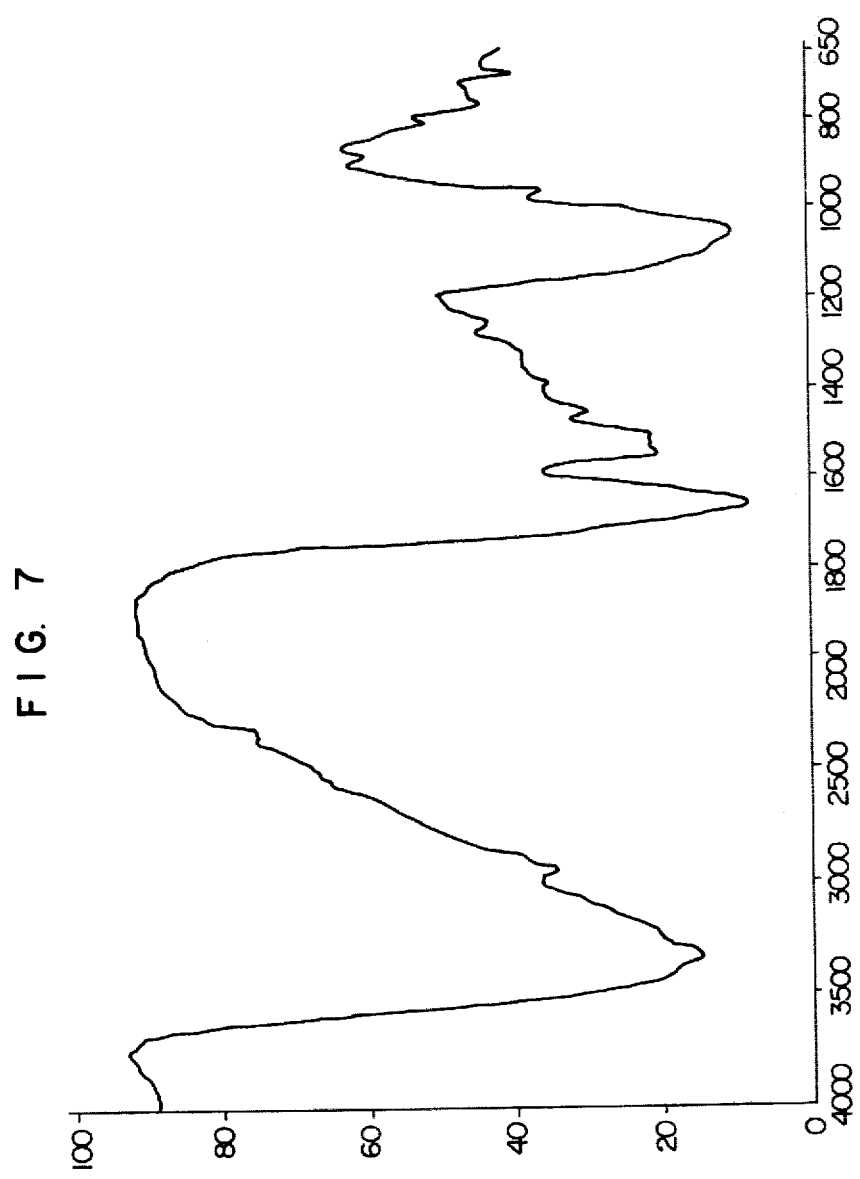
Figure 8:
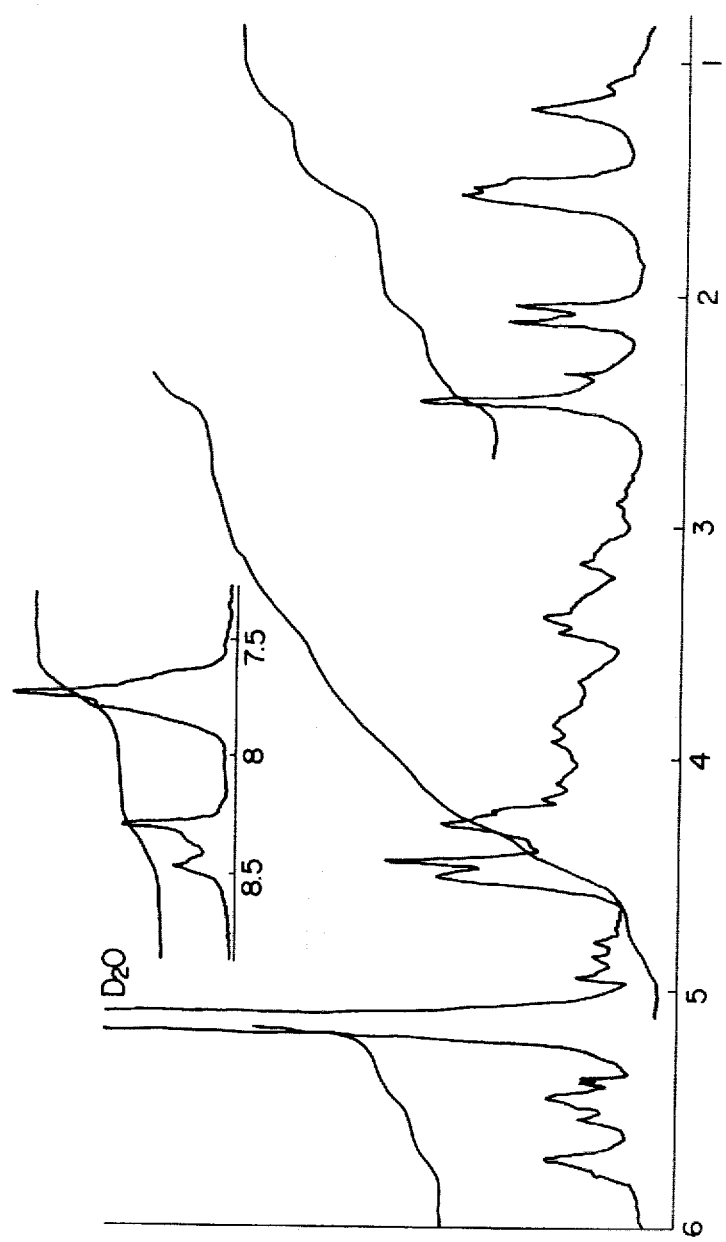

An object of this invention is to provide novel cleomycins represented by the formula

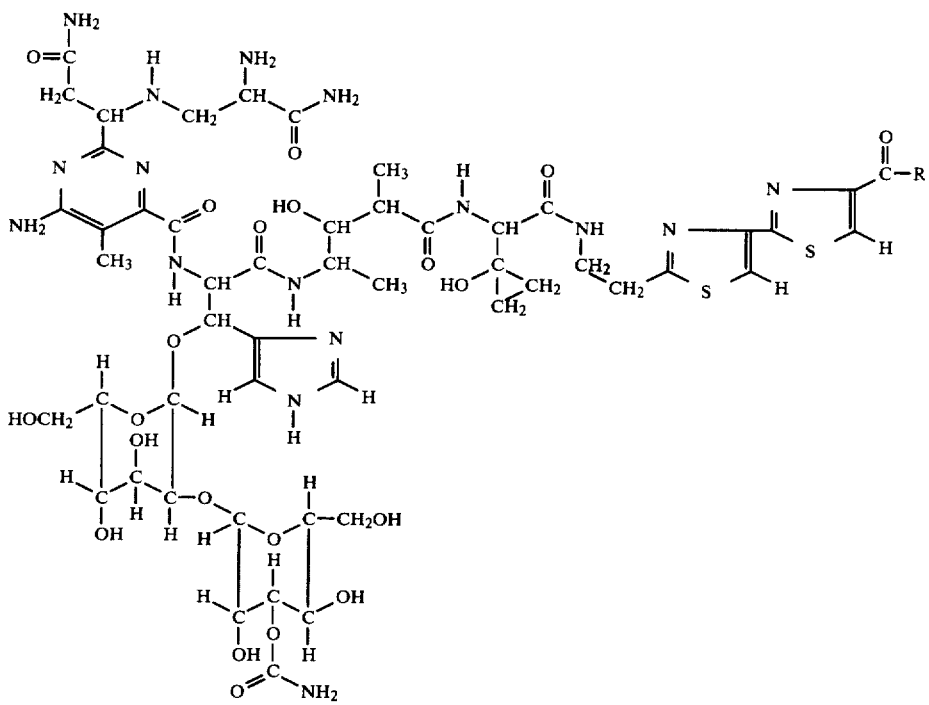

(I)

wherein R represents a terminal amino residue of the cleomycin, and a process for producing said cleomycins. Other objects and advantages of this invention will become apparent from the following description.

The cleomycins of this invention can be obtained by inoculating a cleomycin-producing strain belonging to an actiomycete, *Streptomyces verticillus*, into a medium, to which, if necessary, an aliphatic primary amine having two or more basic groups is added, cultivating the strain to produce a cleomycin represented by the above formmula (I), and thereafter recovering the cleomycin from the medium.

The microorganism for use in this invention is an actinomycete, *Streptomyces verticillus* which is known as a strain capable of producing an antibiotic, bleomycins [Umezawa et al., Journal of Antibiotics, 19, 200 (1966)], and any strain belonging to this genus can be used. A typical one is *Streptomyces verticillus* Collection No. NK 68-144 (ATCC No. 31307). It is widely known that the antibiotic-producing capability of actionomycetes is liable to be naturally or artificially varied; a mutated strain of *Streptmyces verticillus* having a higher capability to produce cleomycin can be used by producing it in a well-known way, for example, by the interaction of X-ray, ultraviolet ray, or a mutation-inducing agent. The cleomycin-producing strains for use in this invention include, of course, such strains naturally or artificially mutated.

Referring to the cultivation process of this invention, as nutrients for the culture medium, proper combinations of materials are used by selecting them from carbon sources such as starch, starch sirup, glucose, mannose, lactose, maltose, sucrose, inositol, mannitol, glycerol, molasses, and organic acids; inorganic or organic nitrogen sources such as ammonium chloride, ammonium sulfate, ammonium nitrate, sodium nitrate, urea, peptone, meat extract, yeast extract, dry yeast, corn steep liquor, soybean meal, defatted soybean meal, fish meal, casamino acid ® (supplied by Difco Co.), and amino acids; and inorganic salts such as sodium chloride, potassium chloride, phosphates, calcium carbonate, zinc sulfate, and copper sulfate.

Cleomycins can be produced satisfactorily by cultivating the above-mentioned strain in the abovementioned medium. However, usually several kinds of cleomycin having different terminal amino residues are incidentally produced, for example, such as 3-S,S-dimethylmercaptopropylaminocleomycin, 4-guanidinobutylaminocleomycin, and 3-(4-aminobutylamino)propylaminocleomycin. Therefore, in order to promote the production of a desired cleomycin according to necessity, an aliphatic primary amine having two or more basic groups in the molecule may be added in addition to the abovementioned nutrition sources. More specific descriptions on this point are given as follows: An aliphatic amine having two or more basic groups in the molecule (hereinafter referred to simply as "amino compound") is added to the culture medium in a suitable amount, for example, from 0.01 to 1% by weight. It has been found from studies that, during the biosynthesis of cleomycins by a cleomycin-producing strain, the above amino compound is uptaken by the cleomycins, transforming into the terminal amino residue. According to this method, various kinds of cleomycin can be produced by varying kind of the amino compound to be added. Furthermore, the selective production of a given kind of cleomycin is possible by addition of an appropriate amount of an amino compound. This is industrially of great advantage. There is no particular restriction on the amino compound to be added, provided that it is an aliphatic primary amine having two or more basic groups in the molecule. As examples of such amino compounds, there may be given the amino compounds represented by the formula $$X-R_{11}-NH_2 \qquad (II)$$

wherein, $R_{11}$ is alkylene or radical represented by the formula $$-R_{12}-Y_1-R_{13}- \text{ or}$$
$$-R_{12}-Y_1-R_{13}-Y_2-R_{14}-$$

[wherein $R_{12}$, $R_{13}$, and $R_{14}$ are each alkylene, and $Y_1$ and $Y_2$ are each radical represented by the formula

(where $R_1$ is hydrogen or a lower alkyl group) or radical represented by the formula

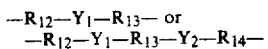

and X has no particular restriction, provided that it is a basic radical, for example, represented by the formula

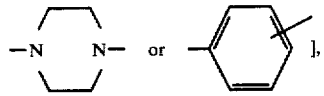

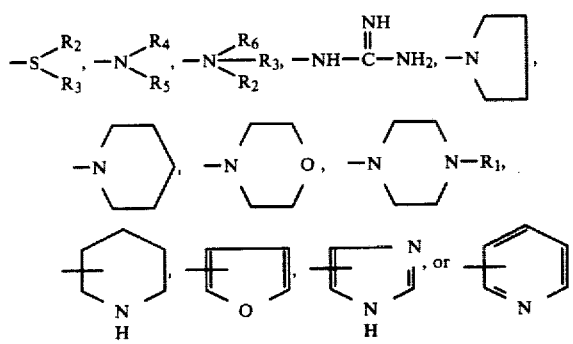

[where $R_1$ is the same as defined above, $R_2$, $R_3$ and $R_6$ are each a lower alkyl group, and $R_4$ and $R_5$ are each hydrogen or an alkyl group]. As examples of the alkylene in the amino compounds, there may be given —CH$_2$—,

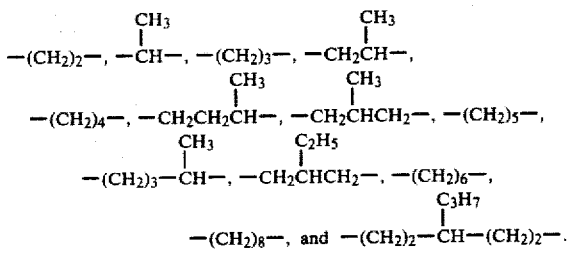

As examples of the lower alkyl group, there may be given methyl, ethyl, propyl, butyl, pentyl, and hexyl groups. And as examples of the alkyl group, there may be given heptyl, octyl group, etc., besides the above-mentioned lower alkyl groups. These lower alkyl groups and alkyl groups may also contain substituents such as a hydroxy group; alkoxy group including methoxy, ethoxy, propoxy, butoxy, and octoxy groups; phenyl group (which may contain a lower alkyl group). Examples of the amino compound and of the cleomycin obtained by the cultivation in the presence of said amino compound are given in Table 1.

Referring to the cultivation process, liquid medium cultivation process and particularly submerged cultivation process are industrially suitable. In the cultivation, a temperature of 20° to 40° C. and a pH value of nearly neutral are desirable. Cleomycins are produced and accumulated in the medium by 2 to 10 days' liquid medium cultivation. The cultivation is stopped when the concentration of cleomycin in the liquid medium reaches a maximum, the mycelium is filtered off, and from the filtrate the intended product is isolated and purified.

Cleomycins have the property to form complexes with cupric ions (hereinafter referred to as "copper-containing form"). In the first place, from the filtrate of culture medium are isolated cleomycins of this copper-containing form, which are easily converted into cleomycins not containing copper (hereinafter referred to as "copper-free form").

TABLE 1

| No. | Name of amino compound to be added | Name of cleomycin and the formula of terminal amino residue |
|---|---|---|
| 1 | 3-aminopropyl-dimethyl-sufonium bromide hydrobromide | 3-s,s-dimethylmercaptopropylamino-cleomycin<br>$\overset{\ominus}{Cl}.(CH_3)_2-\overset{\oplus}{S}-(CH_2)_3-NH-$ |
| 2 | agmatin sulfate | 4-guanidinobutylaminocleomycin<br>$\overset{NH}{\underset{\parallel}{}}$<br>$NH_2-C-NH-(CH_2)_4-NH-$ |
| 3 | 1,2-diaminoethane | 2-aminoethylaminocleomycin<br>$NH_2-(CH_2)_2-NH-$ |
| 4 | 1,3-diaminopropane | 3-aminopropylaminocleomycin<br>$NH_2-(CH_2)_3-NH-$ |
| 5 | 1,4-diaminobutane | 4-aminobutylaminocleomycin<br>$NH_2-(CH_2)_4-NH-$ |
| 6 | spermidine | 3-(4-aminobutylamino)propylamino-cleomycin<br>$NH_2-(CH_2)_4-NH-(CH_2)_3-NH-$ |
| 7 | N,N-dimethyl-1,2-diaminoethane | 2-N,N-dimethylaminoethylaminocleomycin<br>$CH_3$<br>$\phantom{CH_3}\diagdown N-(CH_2)_2-NH-$<br>$CH_3\diagup$ |
| 8 | N,N-diethyl-1,2-diaminoethane | 2-N,N-diethylaminoethlaminocleomycin<br>$C_2H_5$<br>$\phantom{C_2H_5}\diagdown N-(CH_2)_2-NH-$<br>$C_2H_5\diagup$ |
| 9 | N,N-dimethyl-1,3-diaminopropane | 3-N,N-dimethylaminopropylaminocleomycin |

TABLE 1-continued

| No. | Name of amino compound to be added | Name of cleomycin and the formula of terminal amino residue |
|---|---|---|
| 10 | N,N-diethyl-1,3-diaminopropane | 3-N,N-diethylaminopropylaminocleomycin<br>$\underset{CH_3}{\overset{CH_3}{\diagdown}}N-(CH_2)_3-NH-$ |
| 11 | N-n-butyl-N'-(3-aminopropyl)-1,3-diaminopropane | 3-(3-n-butylaminopropylamino)propylaminocleomycin<br>$\underset{C_2H_5}{\overset{C_2H_5}{\diagdown}}N-(CH_2)_3-NH-$ |
| 12 | N-(2-hydroxypropyl)-1,2-diaminoethane | 2-(2-hydroxypropylamino)ethylaminocleomycin<br>$\underset{H}{\overset{C_4H_9}{\diagdown}}N-(CH_2)_3-NH-(CH_2)_3-NH-$ |
| 13 | N-(3-aminopropyl)piperazine | 3-(1-piperazinyl)propylaminocleomycin<br>$CH_3CH(OH)-CH_2\underset{H}{\overset{}{\diagdown}}N-(CH_2)_2-NH-$ |
| 14 | N-(1-phenylethyl)-N'-(3-aminopropyl)-1,3-diaminopropane | 3-[3-(1-phenylethylamino)propylamino]-propylaminocleomycin |
| 15 | 1,2-diaminopropane | 2-aminopropylaminocleomycin<br>$NH_2-CH(CH_3)-CH_2-NH-$ |
| 16 | N-methyl-1,3-diaminopropane | 3-methylaminopropylaminocleomycin<br>$\underset{H}{\overset{CH_3}{\diagdown}}N-(CH_2)_3-NH-$ |
| 17 | N-n-butyl-1,3-diaminopropane | 3-n-butylaminopropylaminocleomycin<br>$\underset{H}{\overset{C_4H_9}{\diagdown}}N-(CH_2)_3-NH-$ |
| 18 | 3-aminopropyl-trimethylammonium chloride | 3-(N,N,N-trimethylamino)propylaminocleomycin<br>$\overset{\ominus}{Cl}\cdot(CH_3)_3\overset{\oplus}{N}-(CH_2)_3-NH-$ |
| 19 | N-[3-(N,N-dimethylamino)propyl]-1,3-diaminopropane | 3-[3-(N,N-dimethylamino)propyl]-propylaminocleomycin<br>$(CH_3)_2N-(CH_2)_3-NH-(CH_2)_3-NH-$ |
| 20 | N,N-bis(3-aminopropyl)methylamine | 3-[N-methyl-N-(3-aminopropyl)]aminopropylaminocleomycin<br>$NH_2-(CH_2)_3-\underset{|}{\overset{CH_3}{N}}-(CH_2)_3-NH-$ |
| 21 | N-(3-amino-1-methylpropyl)-1,3-diaminopropane | 3-(3-amino-1-methylpropylamino)-propylaminocleomycin<br>$NH_2-(CH_2)_2-CH(CH_3)-NH-(CH_2)_3-NH-$ |
| 22 | N-(3-aminopropyl)pyrrolidine | 3-(1-pyrrolidinyl)propylaminocleomycin |
| 23 | N-(3-aminopropyl)piperidine | 3-piperidinopropylaminocleomycin |
| 24 | N-(3-aminopropyl)morpholine | 3-morpholinopropylaminocleomycin |
| 25 | N-(2-aminoethyl)piperazine | 2-(1-piperazinyl)ethylaminocleomycin |
| 26 | N-[3-(1-pyrrolidinyl)propyl]-1,3-diaminopropane | 3-[3-(1-pyrrolidinyl)propylamino]-propylaminocleomycin |

TABLE 1-continued

| No. | Name of amino compound to be added | Name of cleomycin and the formula of terminal amino residue |
|---|---|---|
| 27 | N-(3-piperizinopropyl)-1,3-diaminopropane | 3-(3-piperizinopropylamino)propyl-aminocleomycin<br> |
| 28 | N-(3-morpholinopropyl)-1,3-diaminopropane | 3-(3-morpholinopropylamino)propyl-aminocleomycin<br> |
| 29 | N,N-bis(3-aminopropyl)piperazine | 3-[4-(3-aminopropyl)piperazin-1-yl]-propylaminocleomycin<br> |
| 30 | N-(3-hydroxypropyl)-1,3-diamino-propane | 3-(3-hydroxypropylamino)propylamino-cleomycin<br> |
| 31 | N-(3-methoxypropyl)-1,3-diamino-propane | 3-(3-methoxypropylamino)propylamino-cleomycin<br> |
| 32 | N-benzyl-1,3-diaminopropane | 3-benzylaminopropylaminocleomycin<br> |
| 33 | N-[(s)-1′-phenylethyl]-1,3-diaminopropane | 3-[(s)-1′-phenylethylamino]propyl-aminocleomycin<br> |
| 34 | m-xylylenediamine | m-aminomethylbenzylaminocleomycin<br> |
| 35 | p-xylylenediamine | p-aminomethylbenzylaminocleomycin<br> |
| 36 | N-cyclohexyl-1,3-diaminopropane | 3-cyclohexylaminopropylaminocleomycin<br> |
| 37 | N-(3-cyclohexylaminopropyl)-1,3-diaminopropane | 3-(3-cyclohexylaminopropylamino)-propylaminocleomycin<br> |
| 38 | N-(2-furfuryl)-1,3-diaminopropane | 3-(2-furfurylamino)propylaminocleomycin<br> |
| 39 | 4-piperidylmethylamine | 4-piperidylmethylaminocleomycin<br> |
| 40 | 2-(4-imidazolyl)ethylamine | 2-(4-imidazolyl)ethylaminocleomycin<br> |

TABLE 1-continued

| No. | Name of amino compound to be added | Name of cleomycin and the formula of terminal amino residue |
|---|---|---|
| 41 | N-[2-(2-pyridyl)ethyl]-1,3-diaminopropane | 3-[2-(2-pyridyl)ethylamino]propylamino-cleomycin 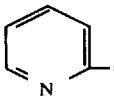 |
| 42 | N-(6-hydroxyhexyl)-1,3-diamino-propane | 3-(6-hydroxyhexylamino)propylamino-cleomycin $HO-(CH_2)_6\diagdown N-(CH_2)_3-NH-$ over $H$ |
| 43 | N-(3-aminopropyl)-1,3-diamino-propane | 3-(3-aminopropylamino)propylamino-cleomycin $NH_2-(CH_2)_3-NH-(CH_2)_3-NH-$ |
| 44 | N-(3-aminopropyl)-1.6-diamino-hexane | 3-(6-aminohexylamino)propylamino-cleomycin $NH_2-(CH_2)_6-NH-(CH_2)_3-NH-$ |
| 45 | N-(3-benzylaminopropyl)-1,3-diaminopropane | 3-(3-benzylaminopropylamino)propyl-aminocleomycin 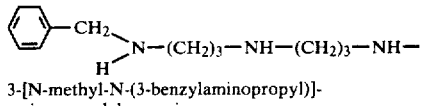 |
| 46 | N-(3-aminopropyl)-N-(3-benzylaminopropyl)-methylamine | 3-[N-methyl-N-(3-benzylaminopropyl)]-aminopropylcleomycin 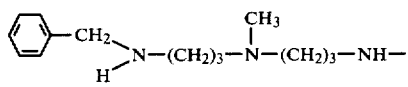 |

For the recovery and purification of cleomycins, all known methods are applicable that are in use for bleomycins, which are analogous in physical and chemical properties to cleomycins. As shown in the following description of the outline, it is carried out by appropriate combination of the known liquid chromatographic techniques. For example, the filtrate of the cultured medium is passed through a column packed with a weakly acidic cation-exchange resin, for example, Amberlite ® IRC-50 (H+ form, supplied by Rohm & Haas Co.), to adsorb the intended substance. After washing of the column with water, the adsorbate is eluted with dilute hydrochloric acid. The fractions that exhibit activity against a test microorganism *Mycobacterium smegmatis* ATCC 607 are collected and neutralized with sodium hydroxide. Then, it is, for the purpose of desalting, passed through a column packed with an adsorption resin of macroreticular type, for example, Amberlite ® XAD-2 (Rohm & Haas Co.) to adsorb the intended substance. After washing of the column with water, the adsorbate is eluted with an aqueous methanol acidified with hydrochloric acid. The active fractions are collected, neutralized with a weakly basic anion-exchange resin, for example, Dowex ® 44 (OH⁻ form, Dow Chem. Corp.), and then evaporated to dryness under reduced pressure. Thus, a desalted crude brownish powder is obtained. It is dissolved in methanol or an aqueous methanol, and the solution is passed through a column packed with neutral alumina using the same solvent. On eluting with the same solvent as the above, bluish green fractions are obtained, and then they are concentrated and dried into a powder. The powder is dissolved in distilled water and passed through a column of Sephadex ® G-25 (Pharmacia Fine Chemicals Inc.). On elution with distilled water, yellow coloring matter is eliminated and blue fractions are obtained. They are dissolved in distilled water again, and passed through a column packed with CM-Sephadex ® C-25 (Na+ form, Pharmacia Fine Chemicals Inc.) using distilled water. Blue fractions containing cleomycins are recovered by eluting with an aqueous solution containing sodium chloride in such a way that the sodium chloride concentration in the eluent is gradually raised up to 1 mol/liter. When two kinds or more of cleomysin are produced, they are separated in the above-mentioned process and recovered separately. These fractions are desalted in the above-mentioned way, which employs Amberlite ® XAD-2, and lyophilized. Thus, a crude blue powder containing cleomycin is obtained.

Usual cleomycin-producing strains produce bleomycins as a by-product. Consequently, the cleomycin powder obtained through the purification steps described above is contaminated with the bleomycin having the same terminal amino residue as that of cleomycin. Hence, the present inventors made extensive studies for a method of obtaining purified cleomycin free from bleomycin. As a result, they have developed a liquid chromatographic method which uses a column packed with an adsorption resin of macroreticular type such as, for example, Amberlite ® XAD-2 or Diaion ® HP-40 (Mitsubishi Chemical Co.) or a column packed with a chemical bonded silica commercially-sold for reversed phase chromatography, such as, for example, LiChroprep ® (E. Merck Inc.), Type RP 8 or Type RP 18 or PrepPak ® 500/C 18 Cartridge (Waters Assoc. Inc.).

Cleomycin has a stronger affinity for the above packing material, as compared with bleomycin having the same terminal amino residue. Accordingly, the development by an appropriate solvent system permits the elimination of bleomycin with eluting it earlier than cleomycin. More specifically, an aqueous solution of the above crude powder is poured into a column packed with a resin, for example, Amberlite ® XAD-2. On developing by distilled water or aqueous methanol, bleomycin is eluted earlier and eliminated. The late eluate containing cleomycin is recovered, concentrated, and lyophilized, whereby a pure cleomycin (copper-containing form) is obtained in the form of blue amorphous powder. When the intermediate eluate containing both cleomycin and bleomycin is returned to the above column to subject again to adsorption and elution (this procedure is hereinafter referred to as "recycle"), an additional amount of pure cleomycin can be recovered. The recycle may be repeated as required.

The methanol concentration of the above eluent is desirably increased in response to the hydrophobicity of cleomycin to be produced, and generally a proper concentration less than 80% (V/V) may be selected. It is effective on enhancement of the separation performance to add to the eluent a salt such as sodium chloride, ammonium chloride, sodium sulfate, ammonium sulfate, sodium acetate, potassium acetate, ammonium acetate, ammonium formate, sodium citrate, sodium dihydrogenpohsphate, disodium hydrogenphosphate, potassium dihydrogenpohsphate, or dipotassium hydrogenphosphate or to add an acid such as hydrochloric acid, sulfuric acid, phosphoric acid, acetic acid, or citric acid for the purpose of pH adjustment.

The method described above is applicable when other types of packing materials, for example, the above-mentioned chemical bonded silica, are used. For example, measured retention times in the reverse phase liquid chromatography of cleomycins (copper-containing form) produced according to the present process are given in Table 2.

TABLE 2

| Compound No. [the same as Table 1] | Retention time (min.) | |
|---|---|---|
| | Solvent 1 | Solvent 2 |
| 1 | | 9.44 |
| 2 | | 14.61 |
| 3 | | 6.47 |
| 4 | | 6.64 |
| 5 | | 8.23 |
| 6 | | 7.39 |
| 11 | 8.52 | 14.78 |
| 12 | | 7.91 |
| 13 | | 11.65 |
| 14 | 14.95 | >30 |
| 18 | | 8.47 |
| 19 | | 9.90 |
| 20 | | 7.38 |
| 21 | | 8.30 |
| 24 | | 9.97 |
| 26 | | 11.55 |
| 28 | | 11.23 |
| 31 | 7.90 | 14.67 |
| 32 | 15.54 | >30 |
| 33 | 21.22 | >30 |
| 37 | 11.40 | 18.65 |
| 40 | | 10.93 |
| 41 | 12.13 | 22.41 |
| 42 | 9.30 | 20.00 |
| 43 | | 6.41 |
| 44 | | 7.45 |
| 45 | 10.24 | 21.61 |
| 46 | 13.50 | >30 |

Note 1.
Chromatographic column: Chemical bonded silica Microbondapack ® C 18 (4 mm × 300 mm, Waters Assoc. Inc.)
Note 2.
Solvent 1: Aqueous solution (containing 1% potassium acetate and 0.5% acetic acid): methanol = 65:35 V/V
Solvent 2: The same aqueous solution as the above: methanol = 70:30 V/V The cleomycin (copper-containing form) thus obtained is freed from copper by a known method, for example, by the method employing EDTA (U.S. Pat. No. 3,929,993) to obtain copper free form thereof.

An example of this method is explained below: The copper-containing form of cleomycin is dissolved in distilled water, and the solution is poured into a column packed with Amberlite ® XAD-2 to adsorb the solutes. The column is washed successively with an aqueous solution containing 2% of sodium chloride and 5% of ethylenediaminetetraacetic acid disodium salt (hereinafter referred to as "EDTA.Na$_2$"), with an aqueous solution containing 2% of sodium chloride to remove excess EDTA.Na$_2$, and with distilled water. Then, by the elution with an acidic aqueous methanol, for example, 0.02 N hydrochloric acid-methanol (1:4 V/V), the fractions exhibiting an ultraviolet absorption maximum near the wavelength 290 m$\mu$ are collected. The collected eluate is adjusted to pH 6.0 using Dowex ® 44 (OH$^-$ type), concentrated under reduced pressure, and lyophilized, giving the copper-free form of cleomycin hydrochloride as a pale yellowish white amorphous powder. When, for example, dilute sulfuric acid is used in place of the above dilute hydrochloric acid, the intended product is obtained in the form of sulfate. A nontoxic salt of cleomycin with an optional but pharmaceutically acceptable acid can be obtained by selecting the acid to be used in the elution step as described above.

The ultraviolet absorption spectra of cleomycins (copper-containing form) produced according to the process of this invention have maxima near the wavelengths 292 m$\mu$ and 243 m$\mu$, which are very close to those of bleomycins. The above-mentioned spectra (hereinafter referred to as "bleomycin type ultraviolet absorption spectra"), in comparison with those of antibiotics belonging to the phleomycin-bleomycin group, are clearly different from those of phleomycins, zorbamycins, and YA-56 substance.

Decomposition products as shown in Table 3 are produced when cleomycins are hydrolyzed with 6 N hydrochloric acid at 105° C. for 24 hours. As can be seen from Table 3, cleomycins are featured in that, unlike bleomycins, they do not produce L-threonine. Concerning to this point, in comparison with other antibiotics giving the bleomycin type ultraviolet absorption spectra, tallysomycin and platomycin produce L-threonine but do not produce 2'-(2-aminoethyl)-2,4'-bithiazol-4-carboxylic acid, and therefore they are clearly different from cleomycins. Zorbonomycins are also clearly different because they produce $\beta$-hydroxy-L-valine, though they do not produce L-threonine. As regard to victomycins, the sulfur-content is only 1.98%, while cleomycins have a sulfur-containing amino acid, 2'-(2-aminoethyl)-2,4'-bithiazol-4-carboxylic acid as a constituent and sulfur content, even in the cleomycin of the minimum sulfur content, is as much as about 4%. From this point, victomycins do not have the above sulfur-containing amino acid and is distinguishable from cleomycins.

TABLE 3

| Acid-catalyzed hydrolysis product | Cleomycin | Bleomycin |
|---|---|---|
| 1. L-threonin | − | + |
| 2. $\beta$-Amino-$\beta$-(4-amino-6-carboxy-5-methylpyrimidine-2-yl)-propionic acid | + | + |
| 3. 4-amino-3-hydroxy-2-methyl-n-pentanoic acid | + | + |
| 4. $\beta$-hydroxy-L-histidine | + | + |
| 5. $\beta$-Amino-L-alanine | + | + |
| 6. 2'-(2-aminoethyl)-2,4'-bithiazole-4-carboxylic acid | + | + |

TABLE 3-continued

| Acid-catalyzed hydrolysis product | Cleomycin | Bleomycin |
|---|---|---|
| 7. Terminal amine | + | + |

In addition, $^{13}$C-NMR and proton-NMR spectra were measured on representative cleomycins produced in the process of this invention. On the basis of these results and of the chemical properties, the chemical structure of cleomycin was investigated and proved to be the novel structure represented by the foregoing formula (I).

The proton NMR spectra were measured on cleomycin samples in heavy water at a frequency of 100 MHz using tetramethylsilane as an external standard, and a broad signal, which is common to cleomycins and corresponds to 4 protons, was observed at a chemical shift $\delta$ of about 1.2 (ppm). This signal was assigned to the methylene group (4 and 5) in the partial structure represented by the novel formula (III):

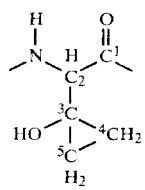

It was found that this partial structure is decomposed by the above-mentioned hydrolysis into 1-amino-2-butanone through cleavage of the cyclopropane ring and decarboxylation.

The $^{13}$C-NMR spectra of cleomycins were measured at a frequency of 25.2 MHz in heavy water using dioxane as an internal standard. As a typical example thereof, those of 3-[(s)-1'-phenylethylamino]-propylaminocleomycin are shown as follows: As signals which are common to cleomycins and assignable to fundamental structure thereof, the following 51 signals emanating from carbon atoms were observed: ($\delta$) 178.0, 176.9, 172.1, 172.0, 171.0, 169.8, 168.5, 166.1, 165.4, 163.8, 163.1, 158.7, 153.0, 149.3, 147.6, 137.6, 135.4, 125.7, 119.9, 118.6, 113.1, 99.0, 98.3, 75.4, 75.2, 74.4, 73.8, 71.2, 70.0, 69.2, 68.8, 67.9, 65.6, 61.8, 61.2, 60.4 (x2), 57.8, 56.3, 53.3, 48.3, 47.7, 43.6, 40.9, 39.9, 32.9, 15.6, 12.7 (x3), and 11.7. In addition, as signals ($\delta$) assignable to the terminal amino residue, 136.2, 130.3, 130.1 (x2), 128.3 (x2), 59.0, 45.3, 37.0, 26.3, and 19.3 were observed. That is, 62 signals in all, emanating from carbon atoms, were observed. These data were analyzed with reference to the signals of bleomycins reported in the literature [Naganawa, et al., Journal of Antibiotics, 30, 388 (1977)]. The results have supported formula (I). With respect to the partial structural formula (III), the following assignment was made.

172.1 (1), 56.3 (3), 60.4 (2), 12.7×2 (4 and 5) wherein numbers in parentheses denote the position numbers of the corresponding carbon atoms, respectively.

Physical and chemical properties of typical cleomycins are summarized in Table 4.

Typical examples of the biological activities measured on cleomycins (copper-free form) are illustrated below.

(1) Antimicrobial activity

Comparison was made with the relevant antibiotics bleomycins. The relative antimicrobial potency (u/mg) against *Mycobacterium smegmatis* ATCC 607 was measured by agar plate-cylinder method using bleomycin $A_2$ as a standard (1,000 u/mg). The results are given in Table 5.

TABLE 4-1

| Physical and chemical properties | Compound (copper-containing form) (refer to Table 1) | | | | |
|---|---|---|---|---|---|
| | Cleomycin No. 1 hydrochloride | Cleomycin No. 2 hydrochloride | Cleomycin No. 11 hydrochloride | Cleomycin No. 20 hydrochloride | Cleomycin No. 33 hydrochloride |
| (1) Appearance | Blue amorphous powder | Blue amorphous powder | Blue amorphous powder | Blue amorphous powder | Blue amorphous powder |
| (2) Solubility | Soluble in water, dimethylformamide, dimethylsulfoxide, and methanol | Soluble in water, dimethylformamide, dimethylsulfoxide, and methanol | Soluble in water, dimethylformamide, dimethylsulfoxide, and methanol | Soluble in water, dimethylformamide, dimethylsulfoxide, and methanol | Soluble in water, dimethylformamide, dimethylsulfoxide, and methanol |
| (3) Color reaction | Positive to Dragendorff, Ehrlich, Pauly, Rydon-Smith reagents | The same as the left. In addition, positive to Sakaguchi reagent | The same as cleomycin No. 1 | The same as cleomycin No. 1. In addition, positive to ninhydrin reagent | The same as cleomycin No. 2 |
| (4) Molecular formula and molecular weight | $C_{56}H_{83}N_{17}S_3O_{21}Cl_2Cu$ | $C_{56}H_{84}N_{20}O_{21}S_2Cl_2Cu$ | $C_{61}H_{96}N_{19}O_{21}S_2Cl_3Cu$ | $C_{58}H_{90}N_{19}O_{21}S_2Cl_1Cu$ | $C_{62}H_{88}N_{18}O_{21}S_2Cl_2Cu$ |
| | 1561.01 | 1571.97 | 1665.57 | 1623.49 | 1620.06 |
| (5) Melting point (decomp.) (°C.) | 205–208 | 197–201 | 189–192 | 193–195 | 203–205 |
| (6) Ultraviolet absorption maxima (in distil. water) Wavelength mμ (molecular extinction coefficient ε) | 292 (1.81 × 10$^4$) | 292 (1.89 × 10$^4$) | 292 (1.83 × 10$^4$) | 292 (1.91 × 10$^4$) | 292 (1.90 × 10$^4$) |
| | 243 (2.25 × 10$^4$) | 243 (2.34 × 10$^4$) | 243 (2.25 × 10$^4$) | 243 (2.35 × 10$^4$) | 243 (2.32 × 10$^4$) |
| (7) Circular dichroism (in distil. water) $[\theta]_\lambda^{27}$ (°), wavelength λ (mμ) | 0 (230) | 0 (230) | 0 (230) | 0 (230) | −4,000 (230) |
| | +27,000 (253) | +25,000 (253) | +26,000 (253) | +26,000 (253) | +26,000 (253) |
| | −14,000 (312) | −13,000 (312) | −10,000 (314) | −14,000 (312) | −14,000 (312) |
| | +4,100 (565) | +4,200 (565) | +3,500 (565) | +4,500 (562) | +4,600 (565) |
| | −1,700 (678) | −1,700 (678) | −1,400 (678) | −1,800 (674) | −1,900 (678) |
| (8) Thin layer chromatography, Rf value | (1) 0.43 | (1) 0.79 | (1) 0.35 | (1) 0.24 | (1) 0.78 |

TABLE 4-1-continued

| Physical and chemical properties | Compound (copper-containing form) (refer to Table 1) | | | | |
|---|---|---|---|---|---|
| | Cleomycin No. 1 hydrochloride | Cleomycin No. 2 hydrochloride | Cleomycin No. 11 hydrochloride | Cleomycin No. 20 hydrochloride | Cleomycin No. 33 hydrochloride |
| (see Note 1) | (2) 0.53 | (2) 0.64 | (2) 0.71 | (2) 0.46 | (2) 0.78 |
| (9) Relative electrophoretic mobility, Rm value (Rm of L-alanine = 1) (see Note 2) | 0.88 | 0.82 | 1.09 | 1.06 | 0.85 |

Note 1
(a) Silica gel 60F 254 ® (Merck Inc.), methanol-10% aq. ammonium acetate-10% aq. ammonia (10:9:1 v/v)
(b) Avicel SF ® (FMC Corp.), n-propanol-pyridine-acetic acid-water (15:10:3:12 v/v)
Note 2
Avicel SF ®, formic acid-acetic acid-water (25:75:900 v/v), 800 V, 15 minutes

TABLE 4-2

| Physical and chemical properties | Compound (copper-free form) (refer to Table 1) | | | | |
|---|---|---|---|---|---|
| | Cleomycin No. 1 hydrochloride | Cleomycin No. 2 hydrochloride | Cleomycin No. 11 hydrochloride | Cleomycin No. 20 hydrochloride | Cleomycin No. 33 sulfate |
| (1) Appearance | Pale yellowish white amorphous powder | Pale yellowish white amorphous powder | Pale yellowish white amorphous powder | Pale yellowish white amorphous powder | Pale yellowish white amorphous powder |
| (2) Solubility | Soluble in water, dimethylformamide, dimethylsulfoxide, and methanol | Soluble in water, dimethylformamide, dimethylsulfoxide, and methanol | Soluble in water, dimethylformamide, dimethylsulfoxide, and methanol | Soluble in water, dimethylformamide, dimethylsulfoxide, and methanol | Soluble in water, dimethylformamide and dimethyl-sulfoxide |
| (3) Color reaction | Positive to Dragendorff, Ehrlich, Pauly, Rydon-Smith, and ninhydrin reagents | The same as the left. In addition, positive to Sakaguchi reagent | The same as cleomycin No. 1 | The same as cleomycin No. 1 | The same as cleomycin No. 1 |
| (4) Molecular formula and molecular weight | $C_{56}H_{85}N_{17}S_3O_{21}Cl_2$ 1499.47 | $C_{56}H_{86}N_{20}O_{21}S_2Cl_2$ 1510.44 | $C_{61}H_{98}N_{19}O_{21}S_2Cl_3$ 1604.04 | $C_{58}H_{92}N_{19}O_{21}S_2Cl_3$ 1561.96 | $C_{62}H_{90}N_{18}O_{25}S_3$ 1583.68 |
| (5) Melting point (decomp.) (°C.) | 182–185 | 185–188 | 172–175 | 193–195 | 189–191 |
| (6) Ultraviolet absorption maxima (in 0.1 N NCl) Wavelength, mμ (molecular extinction coefficient ε) | 290 (1.67 × 10⁴) 240 (2.17 × 10⁴) (shoulder) | 290 (1.63 × 10⁴) 240 (2.19 × 10⁴) (shoulder) | 290 (1.64 × 10⁴) 240 (2.10 × 10⁴) (shoulder) | 289 (1.69 × 10⁴) 240 (2.19 × 10⁴) (shoulder) | 290 (1.62 × 10⁴) 240 (2.09 × 10⁴) (shoulder) |
| (7) Circular dichroism (in 0.1 N HCl) $[\theta]_\lambda^{27}$ (°) wavelength λ mμ | −16,000 (230) +2,600 (290) −700 (320) | −15,000 (230) +2,500 (290) −500 (320) | −15,000 (230) +2,500 (290) −700 (320) | −15,000 (230) +2,600 (290) −500 (320) | −19,000 (230) +2,300 (290) −600 (320) |
| (8) Thin layer chromatography, Rf value (see Note 1) | (1) 0.39 (2) 0.42 | (1) 0.69 (2) 0.58 | (1) 0.26 (2) 0.65 | (1) 0.20 (2) 0.37 | (1) 0.70 (2) 0.70 |
| (9) Relative electrophoretic mobility, Rm value (Rm of L-alanine = 1) (see Note 2) | 1.00 | 0.98 | 1.16 | 1.17 | 0.97 |

Note 1
(a) Silica gel 60 F 254 ® (Merck Inc.), methanol-10% aq. ammonium acetate-10% aq. ammonia (10:9:1 v/v)
(b) Avicel SF ® (FMC Corp.), n-propanol-pyridine-acetic acid-water (15:10:3:12 v/v)
Note 2
Avicel SF ®, formic acid-acetic acid-water (25:75:900 v/v), 800 V, 15 minutes.

TABLE 5

| Compound No. (cf. Table 1) | Antimicrobiral potency (u/mg) |
|---|---|
| 1 | 1,320 |
| 2 | 3,262 |
| 3 | 2,760 |
| 4 | 2,150 |
| 5 | 1,935 |
| 6 | 3,575 |
| 11 | 7,942 |
| 12 | 2,280 |
| 13 | 980 |
| 14 | 11,420 |
| 18 | 878 |
| 19 | 2,004 |
| 20 | 2,273 |
| 21 | 2,620 |
| 24 | 800 |
| 26 | 3,590 |
| 28 | 1,715 |
| 31 | 1,869 |
| 32 | 6.977 |
| 33 | 10,949 |
| 37 | 14,784 |
| 40 | 1,147 |
| 41 | 6,068 |
| 42 | 4,806 |
| 43 | 2,790 |
| 44 | 3,520 |
| 45 | 8,400 |
| 46 | 7,660 |

(2) Activity on cultured HeLa $S_3$ cells

Fifty percent inhibitory cocentration ($LD_{50}$) was determined on a test compound cleomycin (No. 33) and on a reference compound bleomycin $A_2$, from the percent of growth inhibition measured on HeLa $S_3$ cells after the cells had been cultured in the presence of each of the compounds. The results are given in Table 6.

TABLE 6

| Compound (copper-free hydrochloride) | $LD_{50}$ ($\mu$g/ml) |
|---|---|
| Bleomycin $A_2$ (reference compound) | 0.73 |
| Cleomycin No. 33 | 0.77 |

As can be seen from the results mentioned above, cleomycins have antimicrobial activity not inferior at all to the reference compound bleomycin $A_2$. With respect to anti-HeLa action, cleomycin No. 33, a representative cleomycin, has an activity nearly equal to that of bleomycin $A_2$, which is now in use for the clinical treatment of squamous cell carcinoma. These results suggest the usefulness of cleomycins as a chemotherapeutic agent for treating bacterial infections or cancer.

The present invention is illustrated in more detail by the following examples, but is not limited to these examples.

EXAMPLE 1

Production of
3-[(s)-1'-phenylethylamino]-propylaminocleomycin

Step A

*Streptmyces verticillus* NK 68-144 (ATCC 31307) cultivated in an agar slant medium was inoculated in a seed medium (pH 7.0) containing 2% of glucose, 0.3% of sodium chloride, 0.75% of peptone, and 0.75% of meat extract, and was subjected to shaking culture at 27° C. for 24 hours to obtain a seed culture. A production culture medium (120 l, pH 7.0) containing 10% of starch sirup, 1% of glucose, 5% of soybean meal, 1% of corn steep liquor, 0.3% of sodium chloride, 0.1% of dipotassium hydrogenphosphate, 0.05% of zinc sulfate (heptahydrate), 0.05% of copper sulfate (pentahydrate), and 0.2% of sodium nitrate was sterilized in a 200-liter capacity stainless steel tank, and inoculated with 2.5% by volume of the above-mentioned seed culture. Successively, 0.1% based on the medium of N-[(s)-1'-phenylethyl]-1,3-diaminopropane was added thereto. After cultivation at 27° C. for 187 hours under aeration and stirring, the cultivation was stopped, and the medium was filtered using a filter aid to obtain a 115 l culture filtrate. After adjusted with hydrochloric acid to pH 7.0, it was passed through a 7-liter column packed with Amberlite ® IRC-50 (H+ form) to adsorb the intended substance. After washing with water, the adsorbate was eluted with 0.5 N hydrochloric acid. The fractions active against *Mycobacterium smegmatis* ATCC 607 were collected, and neutralized with 1 N sodium hydroxide.

Then, it was passed through a 2-liter column packed with Amberlite ® XAD-2 to adsorb the intended substance. After washing with water, the adsorbate was eluted with a mixture of 0.01 N hydrochloric acid and methanol (1:4 V/V) to collect active fractions. The collected fractions were neutralized with Dowex ® 44 (OH− form), evaporated and dried under reduced pressure, and the residue was subjected to extraction with methanol. The methanol soluble portion was passed through a 400-ml column packed with a neutral alumina by use of methanol containing 20% (V/V) of water. By elution with the above solvent, bluish green fractions were collected and evaporated to dryness under reduced pressure. The residue was dissolved in 100 ml of distilled water and passed through a 2-liter column packed with Sephadex ® G-25. The adsorbate was eluted with distilled water, and blue fractions were collected and passed through a 2-liter column packed with CM-Sephadex ® C-25 (Na+ form) to adsorb the intended substance. The adsorbate was eluted with aqueous sodium chloride solution in such a way that the sodium chloride concentration in the eluent is gradually raised up to 1 mol/liter, and the blue fractions flowing out at sodium chloride concentrations around 0.45 mol/liter were collected. The collected fractions were desalted in the above-mentioned way, which employs Amberlite ® XAD-2 and then evaporated to dryness. Thus, 11.7 g of a crude blue powder was obtained.

10 g of the above blue powder was dissolved in distilled water, and the resulting solution was poured into a column of Amberlite ® XAD-2 (1.4 liter volume) equilibrated in advance with a developing solvent, a mixture of 0.02 mol/liter aqueous acetic acid-methanol (75:25 V/V). The column was developed with the above solvent. The bleomycin-containing fractions which were more easily detected by means of an ultraviolet detector were eliminated, the late eluate fractions containing the intended substance were recovered, and the intermediate fractions were "recycled". This developing procedure was repeated 7 times, and the fractions containing the intended substance were recovered in each cycle. All of the recovered fractions were combined together and neutralized with 1 N sodium hydroxide. It was desalted in the above-mentioned way, which employs Amberlite ® XAD-2, concentrated under reduced pressure, and then lyophilized. Thus, 3.2 g of intended product (copper-containing form) hydrochloride was obtained as a blue amorphous powder.

The ultraviolet absorption maxima and antimicrobial potency of this product were as follows:

| Ultraviolet absorption maxima: | |
|---|---|
| Wavelength m$\mu$ | ($E\,^{1\%}_{1\,cm}$, in distilled water) |
| 292 | (117) |
| 243 | (143) |
| Antimicrobial potency: | 11,300 u/mg |

(Note: The antimicrobial potency was determined by taking bleomycin $A_2$ as 1,000 $\mu$/mg and using *Mycobacterium smegmatis* ATCC 607 as a test bacterium. Herinafter, the same was applied.)

Step B 3 g of the copper-containing form product obtained in the preceding Step A was dissolved in 50 ml of distilled water and in order to remove copper, the solution was poured into a column (500 ml) of Amberlite ® XAD-2. The column was washed successively with 1 liter of aqueous solution containing 2% of sodium chloride and 5% of EDTA.$Na_2$, with 1 liter of 2% aqueous sodium chloride, and with 1 liter of distilled water. Then, the adsorbate was eluted with a mixture of 0.02 N sulfuric acid-methanol (1:4 V/V), and fractions having an absorption maximum around a wavelength of 290 m$\mu$ were collected. The collected solution was adjusted with an anion exchange resin Dowex ® 44 (OH− form) to pH 6.0, and then concentrated under reduced pressure, and lyophilized. Thus, 2.6 g of the intended product (sulfate in copper-free form) was obtained as a pale yellowish white amorphous powder in 90% yield.

The ultraviolet absorption maxima and anti-microbial potency of this product were as follows:

| Ultraviolet absorption maxima: | |
|---|---|
| mμ | ($E_{1\ cm}^{1\%}$, in 0.1 N HCl) |
| 290 | (102) |
| 240 (shoulder) | (132) |
| Antimicrobial potency: | 10,949 u/mg |

EXAMPLE 2

Production of 3-[N-methyl-N-(3-aminopropyl)]-aminopropylaminocleomycin

Step A

Liquid medium cultivation, as described in Step A of Example 1, was carried out with addition of 0.1% on the medium of N,N-bis(3-aminopropyl)-methylamine as an amino compound.

From the filtrate of the cultured medium, 13.2 g of a crude blue powder was obtained in the same way as in Step A of Example 1. 5 g of the crude powder was dissolved in distilled water, and the solution was poured into a column (1 l volume) of Amberlite ® XAD-2. On developing with distilled water, most of bleomycin was eluted and a small portion of bleomycin together with the intended substance remained on the resin. The developing solvent was changed to a mixture of 0.01 N hydrochloric acid-methanol (1:4 V/V) to elute the intended substance. The eluate was neutralized with 0.1 N sodium hydroxide, and methanol was distilled off. The residue was again subjected to the chromatography as mentioned above to remove bleomycin. The obtained fractions containing the intended substance were concentrated under reduced pressure and then lyophilized. Thus, 1.2 g of the intended product (hydrochloride in copper-containing form) was obtained as a blue amorphous powder.

The ultraviolet absorption maxima and antimicrobial potency of this product were as follow:

| Ultraviolet absorption maxima: | |
|---|---|
| mμ | ($E_{1\ cm}^{1\%}$, in distilled water) |
| 292 | (118) |
| 243 | (145) |
| Antimicrobial potency: | 2,300 u/mg |

Step B 1 g of the copper-containing form product obtained in the preceding Step A was dissolved in 20 ml of distilled water and freed from copper in the way as described in Step B of Example 1. Thus, 702 mg of the intended product (hydrochloride in copper-free form) was obtained as a pale yellowish white amorphous powder, in 73% yield.

The ultraviolet absorption maxima and antimicrobial potency of this product were as follows:

| Ultraviolet absorption maxima: | |
|---|---|
| mμ | ($E_{1\ cm}^{1\%}$, in 0.1 N HCl) |
| 289 | (108) |
| 240 (shoulder) | (140) |
| Antimicrobial potency: | 2,273 u/mg |

EXAMPLE 3

Production of 3-[N-methyl-N-(3-aminopropyl)]-aminopropylaminocleomycin 100 mg of the crude powder obtained in Step A of Example 2 was dissolved in 5 ml of distilled water, and the solution was poured into a column of LiChroprep ® RP-8 (25 mm × 310 mm) equilibrated in advance with a developing solvent, a mixture of 1% ammonium acetate aqueous solution-methanol (87.5:12.5 V/V). The column was developed with the same developing solvent at a flow rate of 4.25 ml/min. for 7 hours at room temperature. The earlier eluate containing bleomycin was eliminated, and the succeeding eluate containing the intended substance was recovered. It was desalted in the same way by the use of Amberlite ® XAD-2 as described in Step A of Example 1, concentrated, and lyophilized. Thus, 38 mg of the intended product (hydrochloride in copper-containing form) was obtained as a blue amorphous powder.

EXAMPLE 4

Production of 4-guanidinobutylaminocleomycin

Step A

A production culture medium, as described in Step A of Example 1, was placed into 500-ml Erlenmeyer flasks in an amount of each 110 ml, sterilized, and inoculated with 5% by volume of the seed culture mentioned in the same Example. Then, as an amino compound, 0.5% of agmatin sulfate was added thereto.

One hundred of the same samples as mentioned above were prepared and cultured at 27° C. for 8 hours by use of a rotary-shaker. Thereafter, the cultured samples were combined and filtered to obtain 8.5 l of the filtrate of cultured broth.

The filtrate was treated in the same way as used in Step A of Example 1, giving 1.2 g of a crude blue powder. 200 mg of the crude powder was dissolved in 5 ml of distilled water, and the solution was poured into a PrepPak ® 500/C 18 cartridge (5.7 cm × 30 cm) equilibrated in advance with a mixture of an aqueous solution containing 1% of potassium acetate and 0.5% of acetic acid-methanol (7:3 V/V). Then, using a highspeed liquid chromatographic apparatus for preparation, development was carried out by passing the same mixed solvent as mentioned above at a rate of 100 ml/min. for 80 minutes at room temperature. During this development, "recycle" was practiced 3 times and fractions of the intended substance were recovered. The recovered solution was desalted in the same way employing Amberlite ® XAD-2 as in Step A of Example 1, concentrated, and lyophilized. Thus, 80 mg of the intended product (hydrochloride in copper-containing form) was obtained as a blue amorphous powder.

The ultraviolet absorption maxima and antimicrobial potency of this product were as follows:

| Ultraviolet absorption maxima: | |
|---|---|
| mμ | ($E_{1\ cm}^{1\%}$, in distilled water) |
| 292 | (120) |

| -continued | |
|---|---|
| 243 | (152) |
| Antimicrobial potency: | 3,350 u/mg |

Step B 70 mg of the copper-containing form product obtained in the preceding Step A was dissolved in 2 ml of distilled water and freed from copper in the same way as mentioned in Step B of Example 1. Thus, 60 mg of the intended product (hydrochloride in copper-free form) was obtained as a pale yellowish white amorphous powder, in 89% yield.

The ultraviolet absorption maxima and antimicrobial potency of this product were as follows:

| Ultraviolet absorption maxima: | |
|---|---|
| mμ | (E $\frac{1\%}{1 \text{ cm}}$, 0.1 N HCl) |
| 290 | (109) |
| 240 (shoulder) | (146) |
| Antimicrobial potency: | 3,262 u/mg |

EXAMPLE 5

Production of 3-S,S-dimethylmercaptopropylaminocleomycin

Step A

Liquid medium cultivation, as described in Step A of Example 4, was carried out with addition of 0.1% on the medium of 3-aminopropyl-dimethylsulfonium bromide.hydrobromide as an amino compound.

From the filtrate of the cultured broth, 1.6 g of a crude blue powder was obtained in the same way as described in Step A of Example 1. By treating 200 mg of the crude powder in the same way as described in Example 4, 76 mg of the intended product (hydrochloride in copper-containing form) was obtained as a blue amorphous powder.

The ultraviolet absorption maxima and antimicrobial potency of this product were as follows:

| Ultraviolet absorption maxima: | |
|---|---|
| mμ | (E $\frac{1\%}{1 \text{ cm}}$, in distilled water) |
| 292 | (117) |
| 243 | (145) |
| Antimicrobial potency: | 1,360 u/mg |

Step B 70 mg of the copper-containing form product obtained in the preceding Step A was dissolved in 2 ml of distilled water and freed from copper in the same was as described in Step B of Example 1. Thus, 61 mg of the intended product (hydrochloride in copper-free form) was obtained as a pale yellowish white amorphous powder, in 91% yield.

The ultraviolet absorption maxima and antimicrobial potency of this product were as follows:

| Ultraviolet absorption maxima: | |
|---|---|
| mμ | (E $\frac{1\%}{1 \text{ cm}}$, in 0.1 N HCl) |
| 290 | (112) |

| -continued | |
|---|---|
| 240 (shoulder) | (146) |
| Antimicrobial potency: | 1,320 u/mg |

EXAMPLE 6

Production of 3-S,S-dimethylmercaptopropylaminocleomycin

Liquid medium cultivation, as described in Step A of Example 1, was carried out without addition of any amino compound.

From the filtrate of the cultured medium, 6.7 g of the intended product, 3.7 g of 4-guanidinobutylaminocleomycin, and 320 mg of 3-(4-aminobutylamino)-propylaminocleomycin were obtained each as a crude blue powder, by the same treatment as described in Step A of Example 1. By treating 200 mg of crude powder of the intended product in the same way as described in Example 4, 68 mg of the intended product (hydrochloride in copper-containing form) was obtained as a blue amorphous powder.

EXAMPLE 7

Production of 4-guanidinobutylaminocleomycin

The intended product (hydrochloride in copper-containing form) was obtained by treating 200 mg of the intended product crude powder obtained in Example 6, in the same way as described in Example 4.

EXAMPLE 8

Production of 3-(4-aminobutylamino)propylaminocleomycin

Step A 70 mg of the intended product (hydrochloride in copper-containing form) was obtained by treating 200 mg of the intended product crude powder obtained in Example 6, in the same way as described in Example 3.

The ultraviolet absorption maxima and antimicrobial potency of this product were as follows:

| Ultraviolet absorption maxima: | |
|---|---|
| mμ | (E $\frac{1\%}{1 \text{ cm}}$, in distilled water) |
| 292 | (119) |
| 243 | (146) |
| Antimicrobial potency: | 3,520 u/mg |

Step B

By removing copper from 50 mg of the copper-containing form product obtained in the preceding Step A in the same way as described in Step B of Example 1, 38 mg of the intended product (hydrochloride in copper-free form) was obtained as a pale yellowish white amorphous powder, in 79% yield.

The ultraviolet absorption maxima and antimicrobial potency of this product were as follows:

| Ultraviolet absorption maxima: | |
|---|---|
| mμ | (E $\frac{1\%}{1 \text{ cm}}$, in 0.1 N HCl) |
| 290 | (98) |
| 240 (shoulder) | (128) |
| Antimicrobial potency: | 3,575 u/mg |

EXAMPLE 9

Production of 3-(3-n-butylaminopropylamino)propylaminocleomycin

Step A

Liquid medium cultivation, as described in Step A of Example 1, was carried out with addition of 0.1% on the medium of N-n-butyl-N'-(3-aminopropyl)-1,3-diaminopropane as an amino compound.

From the filtrate of the cultured medium, 8.3 mg of a crude blue powder was obtained in the same way as in Step A of Example 1. By treating 5 g of the crude powder in the same way as described in Step A of Example 2, 740 mg of the intended product (hydrochloride in copper-containing form) was obtained as a blue amorphous powder.

The ultraviolet absorption maxima and antimicrobial potency of this product were as follows:

| Ultraviolet absorption maxima: | |
|---|---|
| m$\mu$ | (E $\frac{1\%}{1\text{ cm}}$, in distilled water) |
| 292 | (111) |
| 243 | (136) |
| Antimicrobial potency: | 8,130 u/mg |

Step B

In 20 ml of distilled water, was dissolved 700 mg of the copper-containing form product obtained in the preceding Step A, and freed from copper in the same way as described in Step B of Example 1, whereby 525 mg of the intended product (hydrochloride in copper-free form) was obtained as a pale yellowish white amorphous powder, in 78% yield.

The ultraviolet absorption maxima and antimicrobial potency of this product were as follows:

| Ultraviolet absorption maxima: | |
|---|---|
| m$\mu$ | (E $\frac{1\%}{1\text{ cm}}$, in 0.1 N HCl) |
| 290 | (103) |
| 240 (sholder) | (132) |
| Antimicrobial potency: | 7,942 u/mg |

What is claimed is:

1. Novel antibiotics cleomycins represented by the formula

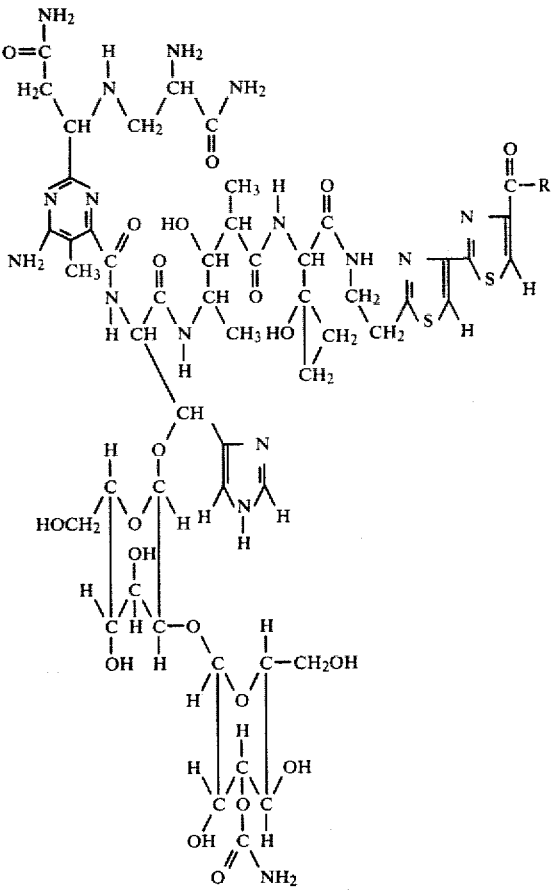

wherein R is a terminal amino residue corresponding to an aliphatic primary amine having at least two basic groups in the molecule, and nontoxic salts thereof selected from the group consisting of hydrochloride and sulfate salts, said basic groups being selected from the group consisting of nitrogen-containing, oxygen-containing and sulfur-containing organic groups.

2. Cleomycins and nontoxic salts thereof selected from the group consisting of hydrochloride and sulfate salts according to claim 1, wherein R is a terminal amino residue corresponding to an aliphatic primary amine having at least two basic groups in the molecule represented by the formula $$X-R_{11}-NH-$$

wherein, $R_{11}$ is an alkylene group having 1 to 8 carbon atoms or a radical represented by the formula $$-R_{12}-Y_1-R_{13}- \text{ or}$$
$$-R_{12}-Y_1-R_{13}-Y_2-R_{14}-$$

wherein $R_{12}$, $R_{13}$, and $R_{14}$ are each an alkylene group having 1 to 8 carbon atoms, and $Y_1$ and $Y_2$ are each radical represented by the formula $$\begin{array}{c} -N- \\ | \\ R_1 \end{array}$$

(where $R_1$ is hydrogen or a lower alkyl group) or a radical represented by the formula

or

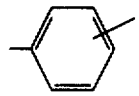

and X is a radical represented by the formula

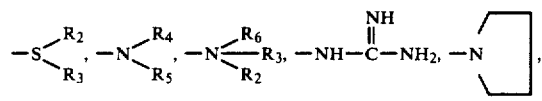

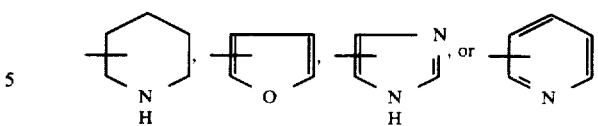

where $R_1$ is the same as defined above, $R_2$, $R_3$, and $R_6$ are each lower alkyl group, and $R_4$ and $R_5$ are each hydrogen or an alkyl group having 1 to 8 carbon atoms.

3. Cleomycins and nontoxic salts thereof selected from the group consisting of hydrochloride and sulfate salts according to claim 1, wherein R is a member selected from the group consisting of

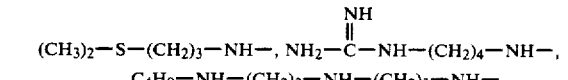

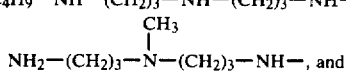

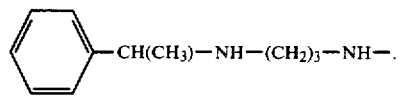

4. 3-S,S-Dimethylmercaptopropylaminocleomycin.
5. 4-Guanidinobutylaminocleomycin.
6. 3-(3-n-Butylaminopropylamino)propylaminocleomycin.
7. 3-[N-Methyl-N-(3-aminopropyl)]aminopropylaminocleomycin.
8. 3-[(S)-1'-Phenylethylamino]propylaminocleomycin.

* * * * *